United States Patent
Peng et al.

(10) Patent No.: US 8,381,603 B2
(45) Date of Patent: Feb. 26, 2013

(54) FALL DETECTION SYSTEM

(75) Inventors: Yang Peng, Shanghai (CN); Sheng Jin, Shanghai (CN)

(73) Assignee: Koninklijke Philips Electronics N.V., Eindhoven (NL)

( * ) Notice: Subject to any disclaimer, the term of this patent is extended or adjusted under 35 U.S.C. 154(b) by 19 days.

(21) Appl. No.: 13/063,051

(22) PCT Filed: Sep. 4, 2009

(86) PCT No.: PCT/IB2009/053867
§ 371 (c)(1),
(2), (4) Date: Mar. 25, 2011

(87) PCT Pub. No.: WO2010/029478
PCT Pub. Date: Mar. 18, 2010

(65) Prior Publication Data
US 2011/0162433 A1    Jul. 7, 2011

(30) Foreign Application Priority Data

Sep. 12, 2008    (CN) .......................... 2008 1 0215978

(51) Int. Cl.
*A61B 5/103*    (2006.01)
(52) U.S. Cl. ......... 73/865.4; 73/1.01; 600/587; 600/595
(58) Field of Classification Search ................... 73/1.01, 73/865.4; 600/587, 595
See application file for complete search history.

(56) References Cited

U.S. PATENT DOCUMENTS

| | | | |
|---|---|---|---|
| 6,307,481 B1 * | 10/2001 | Lehrman et al. | 340/669 |
| 6,433,690 B2 | 8/2002 | Petelenz et al. | |
| 6,703,939 B2 * | 3/2004 | Lehrman et al. | 340/669 |
| 6,864,796 B2 * | 3/2005 | Lehrman et al. | 340/573.1 |
| 6,997,882 B1 * | 2/2006 | Parker et al. | 600/534 |
| 7,095,331 B2 * | 8/2006 | Lehrman et al. | 340/669 |
| 7,145,461 B2 * | 12/2006 | Lehrman et al. | 340/573.1 |
| 7,479,890 B2 * | 1/2009 | Lehrman et al. | 340/573.1 |
| 2002/0008630 A1 * | 1/2002 | Lehrman et al. | 340/669 |
| 2002/0118121 A1 * | 8/2002 | Lehrman et al. | 340/870.16 |
| 2005/0067816 A1 | 3/2005 | Buckman | |
| 2005/0110648 A1 * | 5/2005 | Lehrman et al. | 340/686.1 |
| 2006/0279426 A1 | 12/2006 | Bonnet et al. | |
| 2007/0111753 A1 | 5/2007 | Vock et al. | |
| 2007/0146145 A1 * | 6/2007 | Lehrman et al. | 340/573.1 |
| 2007/0276270 A1 * | 11/2007 | Tran | 600/508 |
| 2008/0016962 A1 | 1/2008 | Dwyer et al. | |

FOREIGN PATENT DOCUMENTS

WO    2008059418 A1    5/2008

* cited by examiner

*Primary Examiner* — Hezron E Williams
*Assistant Examiner* — Rodney T Frank

(57) ABSTRACT

There is provided a fall detection system comprising a fall detector for monitoring the movement of a user and detecting if the user has fallen or is about to fall, one or more sensors for collecting measurements of one or more physical characteristics of the user, wherein the fall detector uses the measurements to adapt the fall detection to the physical characteristics of the user.

16 Claims, 6 Drawing Sheets

FALL DETECTION SYSTEM

TECHNICAL FIELD OF THE INVENTION

The invention relates to a fall detection system, and in particular to a fall detection system that can be configured or adapted to particular physical characteristics of a user.

BACKGROUND TO THE INVENTION

Falls affect millions of people each year and result in significant injuries, particularly in the elderly. In fact, it has been estimated that falls are one of the top three causes of death in elderly people.

A fall is defined as a sudden, uncontrolled and unintentional downward displacement of the body to the ground. There are currently some fall detection systems available that detect these falls and allow the user to obtain assistance manually or automatically if a fall occurs. Exemplary fall detection systems can comprise personal help buttons (PHBs) or worn and/or environment-based automatic detection systems.

Automatic fall detection systems comprise one or a set of sensors that continuously measure the movement of the user, and a processor that compares the measured or processed signals with predetermined thresholds in order to detect a fall. In particular, automatic fall detection systems store a set of predetermined threshold values and/or classification patterns (which are hereinafter referred to as parameter sets). When the system is activated, movement data obtained from the sensors (such as, for example, an accelerometer) will be continuously transformed and processed, and then compared with those parameter sets to determine if a fall event occurs.

Many fall detection systems also calculate a change in the orientation of the fall detection system (and hence the user) and detect an impact with the ground during a fall event.

However, these systems have limitations, since impacts and fall patterns are closely related to the user's weight, and an impact for an old man who weighs 75 kg is quite different from the impact for an old lady who only weighs 45 kg. Therefore, fall detection systems should be adaptive to the size and/or weight of the human body.

Fall detection systems are often designed to be simple for an elderly user to operate, which is why a PHB is only designed with one big button to ease operation. However, it is difficult to use this single button to allow the system to be customized to particular users (for example inputting some personalized body parameters into the fall detection system). Alternative systems that include several buttons and flashing lights or displays may prove to be too complex for an elderly person to operate.

SUMMARY OF THE INVENTION

Therefore, it is an object of the invention to provide a fall detection system that is adaptable to different usage conditions (i.e. for different users), and the predetermined thresholds should be selected appropriately in order to maintain a desired level of detection accuracy. An appropriately selected parameter set and customization to a user helps to enhance the reliability of the fall detection system by increasing detection accuracy and eliminating false positives and false negatives.

It is a further object to make this fall detection system simple and easy to use for an elderly user.

In accordance with a first aspect of the invention, there is provided a fall detection system, comprising a fall detector for monitoring the movement of a user and detecting if the user has fallen or is about to fall; and one or more sensors for collecting measurements of one or more physical characteristics of the user; wherein the fall detector uses the measurements to adapt the fall detection to the physical characteristics of the user.

In accordance with a second aspect of the invention, there is provided a method of operating a fall detection system, the method comprising collecting measurements of one or more physical characteristics of a user of the fall detection system; using the measurements to adapt a detection of falls, or falls that are about to happen, to the physical characteristics of the user.

BRIEF DESCRIPTION OF THE DRAWINGS

The invention will now be described, by way of example only, with reference to the following drawings, in which.

DETAILED DESCRIPTION OF THE PREFERRED EMBODIMENTS

Figure 1:
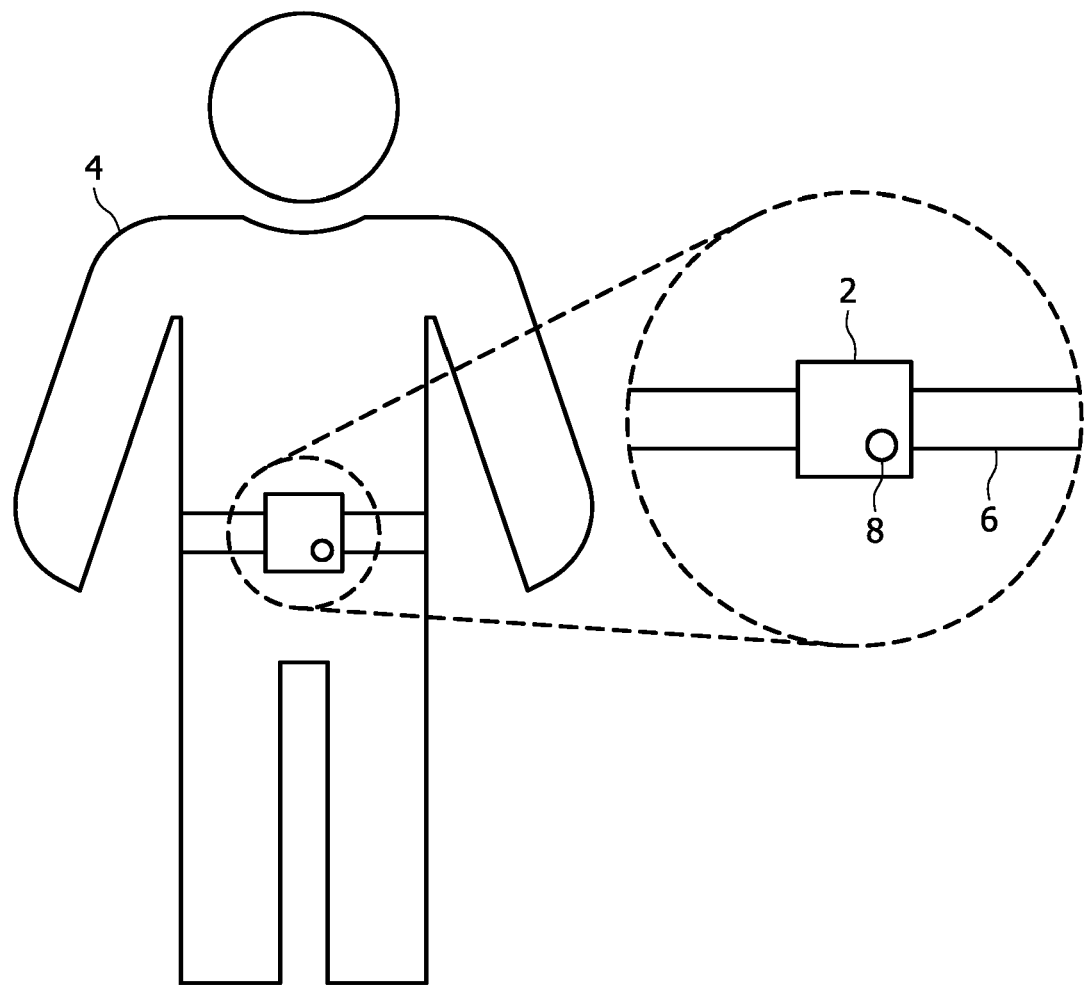
FIG. 1 shows a fall detector attached to a user.

FIG. 1 shows a fall detector 2 attached to a user 4 via a band or other attachment means 6. The fall detector 2 is preferably attached at the upper part of the user's body 4, such as around the waist, at the wrist, or as a pendant around the neck.

In this embodiment, the fall detector 2 includes a button 8 that the user 4 can operate to send an alarm signal to a call-centre or other assistance unit if they fall and require assistance. Thus, this fall detector 2 is of the personal help button (PHB) type described above.

The fall detector 2 comprises one or more sensors for monitoring the movement of the user 4, and a processor for analyzing the signals from the sensors to determine whether the user 4 is about to fall, or whether the user 4 has fallen. The sensors typically include an accelerometer for measuring the acceleration experienced by the fall detector 2. Some fall detectors 2 include a separate sensor for measuring changes in the orientation of the detector 2 (which might occur as the user 4 changes from an upright position to a horizontal position on the ground), although it is possible for an orientation change to be detected by the accelerometer from changes in the direction of gravitational acceleration. Thus, if the z-axis of the accelerometer points upwards perpendicularly to the ground, a change from an upright to horizontal position will be measured as a change from 1 g to 0 g in the z-axis direction.

The processor compares the signals from the sensors with patterns or thresholds that are characteristic of falls, and if the signals indicate that a fall has taken place, an alarm signal is generated.

As described above, as the way in which a user 4 falls (for example the size of the impact generated when they hit the ground) is somewhat dependent on the physical characteristics of the user 4 (for example, their height, weight, age, general physical condition, etc.), it is desirable for the fall detector 2 to be calibrated to take these physical characteristics of the user 4 into account. It is also desirable for this calibration to be effected simply and easily from the point of view of the user 4.

Therefore, a fall detection system is provided that has means for switching the fall detector 2 into a calibration mode and for collecting data on physical characteristics of the user 4. When the fall detector 2 is in the calibration mode, the data collected on the physical characteristics of the user 4 is used to adapt the fall detection to the user 4.

For example, the fall detector 2 can store a plurality of parameter sets for different types of users 4 (so there can be different parameter sets covering variations in height, weight, age, general physical condition, etc.), and the measured physical characteristics can be used to select an appropriate one of the parameter sets to use in detecting falls for the specific user 4.

Figure 2A:
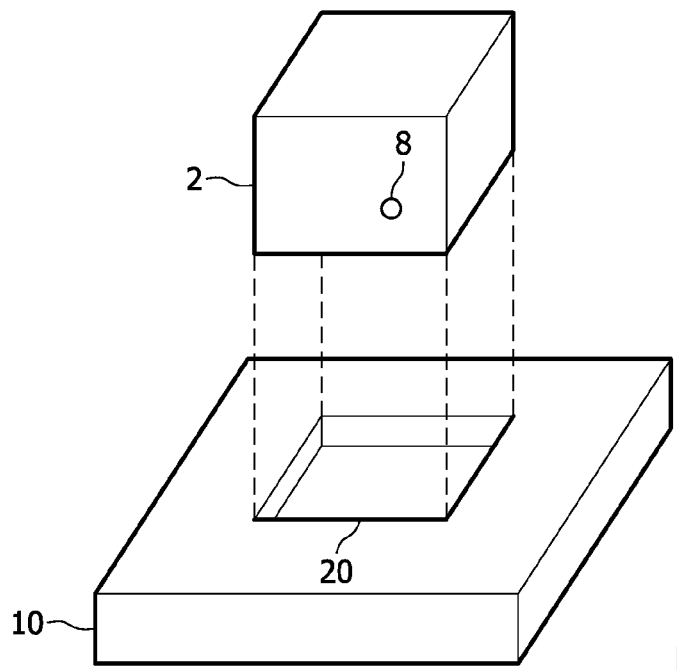
FIGS. 2a and 2b show a fall detection system in accordance with a first embodiment of the invention.
Figure 2B:
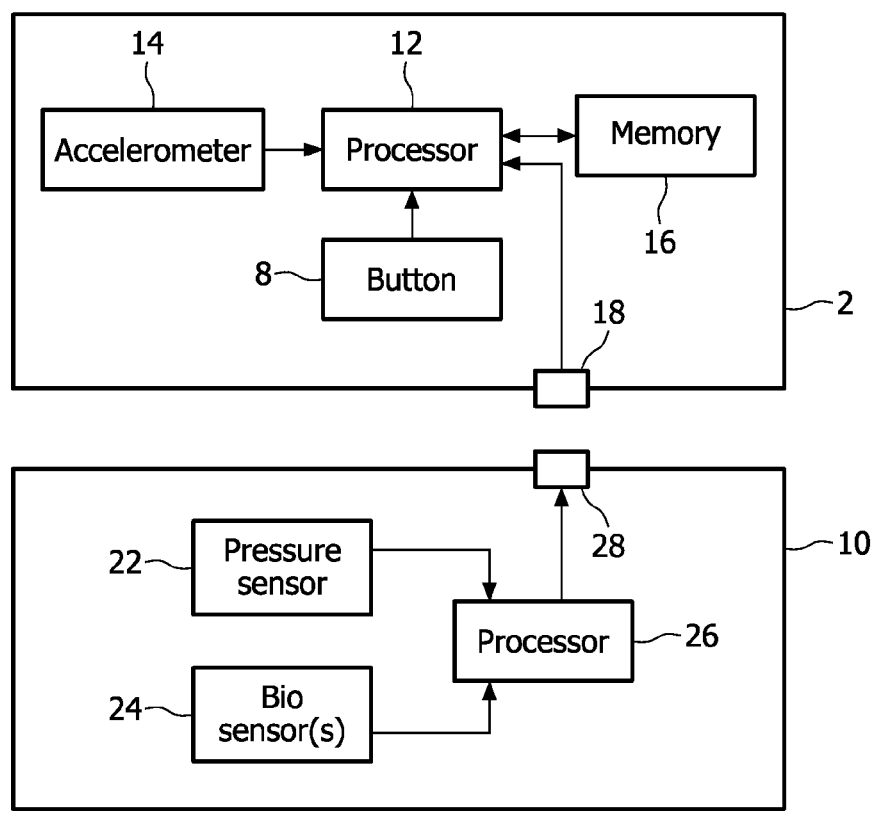

FIGS. 2a and 2b show a first specific embodiment of the invention. In this embodiment, the fall detection system 1 comprises a fall detector 2 as described above, and a calibration unit 10 that includes a means for setting the fall detector 2 into a calibration mode when the fall detector 2 is placed in contact with the calibration unit 10, and sensors for measuring physical characteristics of the user 4.

In particular, the fall detector 2 comprises a processor 12, an accelerometer (and possibly other sensors) 14, a memory 16 and the personal help button 8. The accelerometer 14 measures the acceleration experienced by the fall detector 2 (and hence the user 4) and provides appropriate signals to the processor 12. The memory 16 stores the plurality of parameter sets, as well as any other relevant data (such as any previously measured physical characteristic data for the user 4). The processor 12 uses the signals from the accelerometer 14 (and other sensors if present) and a parameter set from the memory 16 to determine if the user 4 has fallen or is about to fall. The fall detector 2 also includes an interface 18 that enables the fall detector 2 to communicate with (or simply receive information from) the calibration unit 10.

In this embodiment, the calibration unit 10 is in the form of a plate, which has a recess 20 that is shaped to receive part of the housing of the fall detector 2. This way, it will be clear to an elderly user 4 where in the calibration unit 10 the fall detector 2 should be placed.

The calibration unit 10 comprises sensors 22, 24 (and in particular a pressure sensor 22 and biosensors 24) for measuring physical characteristics of the user 4 and a processor 26 for collecting the measurements and providing them to the fall detector 2 via an interface 28 that is adapted to cooperate with the interface 18 on the fall detector 2. The processor 26 can also provide a signal to the fall detector 2 via the interfaces 28, 18 that causes the fall detector 2 to switch into a calibration mode. Alternatively, the fall detector 2 can switch into the calibration mode as soon as it is put into contact with the calibration unit 10 (for example if contact with the calibration unit 10 completes a simple circuit in the fall detector 2).

The calibration unit 10 is constructed so that when the user 4 stands or sits on the unit 10, the pressure sensor 22 measures the weight of the user 4. The calibration unit 10 is further constructed so that when the user 4 stands or sits on the unit 10 or otherwise contacts the calibration unit 10 (such as by holding it), the biosensor(s) 24 measure other physical or physiological characteristics of the user 4, for example including heart rate/pulse, blood pressure, an electrocardiogram (ECG) signal and other biological signals. The calibration unit 10 can be constructed from plastic or other suitable materials.

Figure 3:
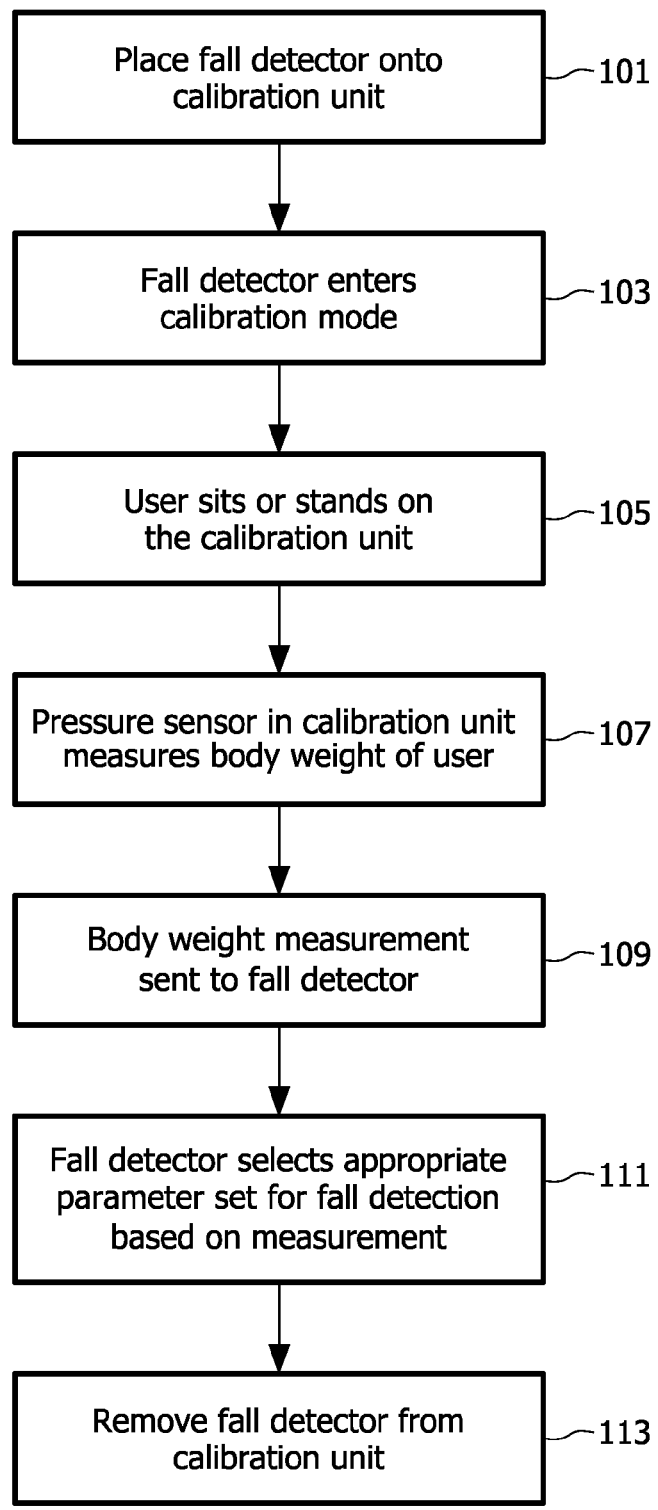
FIG. 3 shows a method in accordance with the first embodiment of the invention.

FIG. 3 shows a method of calibrating a fall detector in accordance with the first embodiment of the invention. The fall detector is placed into contact with, or onto, the calibration unit (step 101) which causes the fall detector to enter the calibration mode (step 103).

The calibration unit and fall detector are then either put on the ground so that the user can stand on the calibration unit, or is placed on a chair or similar so that the user can sit on the calibration unit (step 105).

The pressure sensor in the calibration unit then measures the user's body weight or torso weight if the user sits on the calibration plate (step 107) and this body weight measurement is sent to the fall detector (step 109).

The processor in the fall detector then uses the measured weight to select an appropriate parameter set from the memory for use in subsequent fall detection (step 111).

The calibration method ends (step 113) when the fall detector is removed from the calibration unit, which causes the fall detector to return to (or switch to) a fall detection mode.

As described above, in order to detect falls even more reliably, measurements other than mechanical measurements are also introduced. They are physiological measurements such as blood pressure (BP), heart rate (HR) and ECG. Correlations between mechanical and physiological data can be identified to make the detection accuracy higher. For example, a relationship between syncope and BP/HR change has been identified, which means that appropriate physiological parameter sets can be defined and stored in the memory for use if the measurements of the physical characteristics indicate specific changes in BP or HR. In this case, the biosensors 24 can include a near-infrared (NIR) heart-rate sensor and/or a cuffless BP sensor.

These signals, which are measured only once within a certain period when the user is comfortable (i.e. when the user is standing or sitting on the calibration unit) before the users wear the fall detector, are treated as initial parameters for the algorithm used in fall detection.

This makes the installation or calibration procedure simple and therefore possible for elderly users to perform. Furthermore, it also means that there is no need for biosensors in the fall detector to be in contact with the skin of the user (via electrodes or similar) when the fall detector is in use.

In further embodiments, the fall detector 2 or calibration unit 10 can be provided with a visual or audio indicator that informs the user 4 when the calibration has been completed.

In alternative embodiments, the calibration unit 10 can include a switch which provides the signal that causes the fall detector 2 to switch into the calibration mode. Thus, once the fall detector 2 is placed on the calibration unit 10, the switch can be pressed to put the fall detector into calibration mode.

Figure 4A:
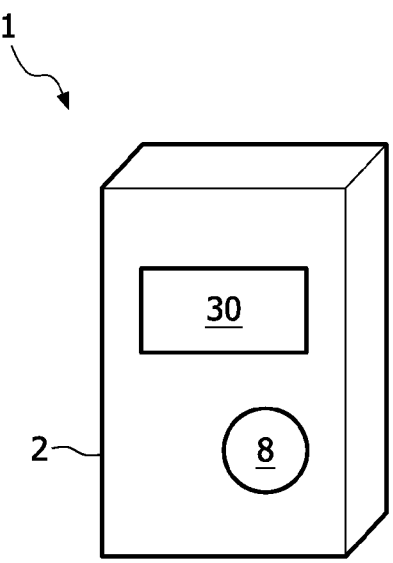
FIGS. 4a and 4b show a fall detection system in accordance with a second embodiment of the invention.
Figure 4B:
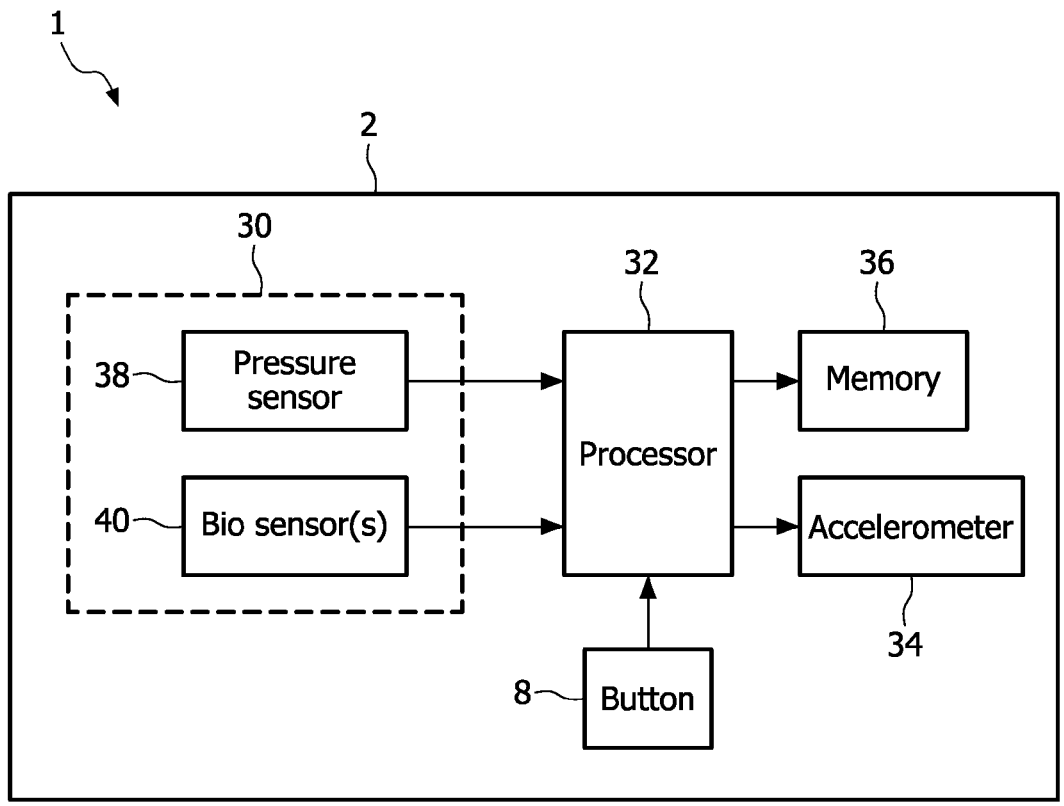

A second specific embodiment of the invention is shown in FIGS. 4a and 4b. In this embodiment, the fall detection system 1 comprises a fall detector 2, but there is no separate calibration unit, so the means for collecting the data on the physical characteristics of the user 4 is also part of the fall detector 2.

As shown in FIG. 4a, the fall detector 2 comprises a personal help button 8, and also a pressure plate 30. The fall detector 2 also comprises a processor 32, an accelerometer (and possibly other movement sensors) 34, a memory 36 and the personal help button 8. As in the first embodiment, the accelerometer 34 measures the acceleration experienced by the fall detector 2 (and hence the user 4) and provides appropriate signals to the processor 32. The memory 36 stores the plurality of parameter sets, as well as any other relevant data (such as any previously measured physical characteristic data for the user 4). The processor 32 uses the signals from the accelerometer 34 (and other sensors if present) and a parameter set from the memory 36 to determine if the user 4 has fallen or is about to fall.

However, in this embodiment, the fall detector 2 includes a pressure plate 30 which is used to put the fall detector 2 into a calibration mode and to measure physical characteristics of the user 4. In particular, the pressure plate 30 has an associated pressure sensor 38 for measuring the pressure or force exerted on the pressure plate 30 by the user 4 and one or more biosensors 40 for measuring other physical or physiological characteristics of the user 4, again including heart rate/pulse, blood pressure, and/or an electrocardiogram (ECG) signal.

If the pressure sensor 38 indicates a pressure that is above a predetermined threshold, the processor 32 will switch the fall detector 2 into the calibration mode. Thus, the pressure sensor 38 and biosensor(s) 40 can measure physical characteristics of the user 4 while the user 4 is holding or pressing the pressure plate 30.

In particular, the degree of strength or frailty of the user 4 can be detected by the amount of pressure exerted on the pressure sensor 38, while the biosensors 40 measure other physical characteristics such as heart rate, blood pressure, ECG, etc.

Figure 5:
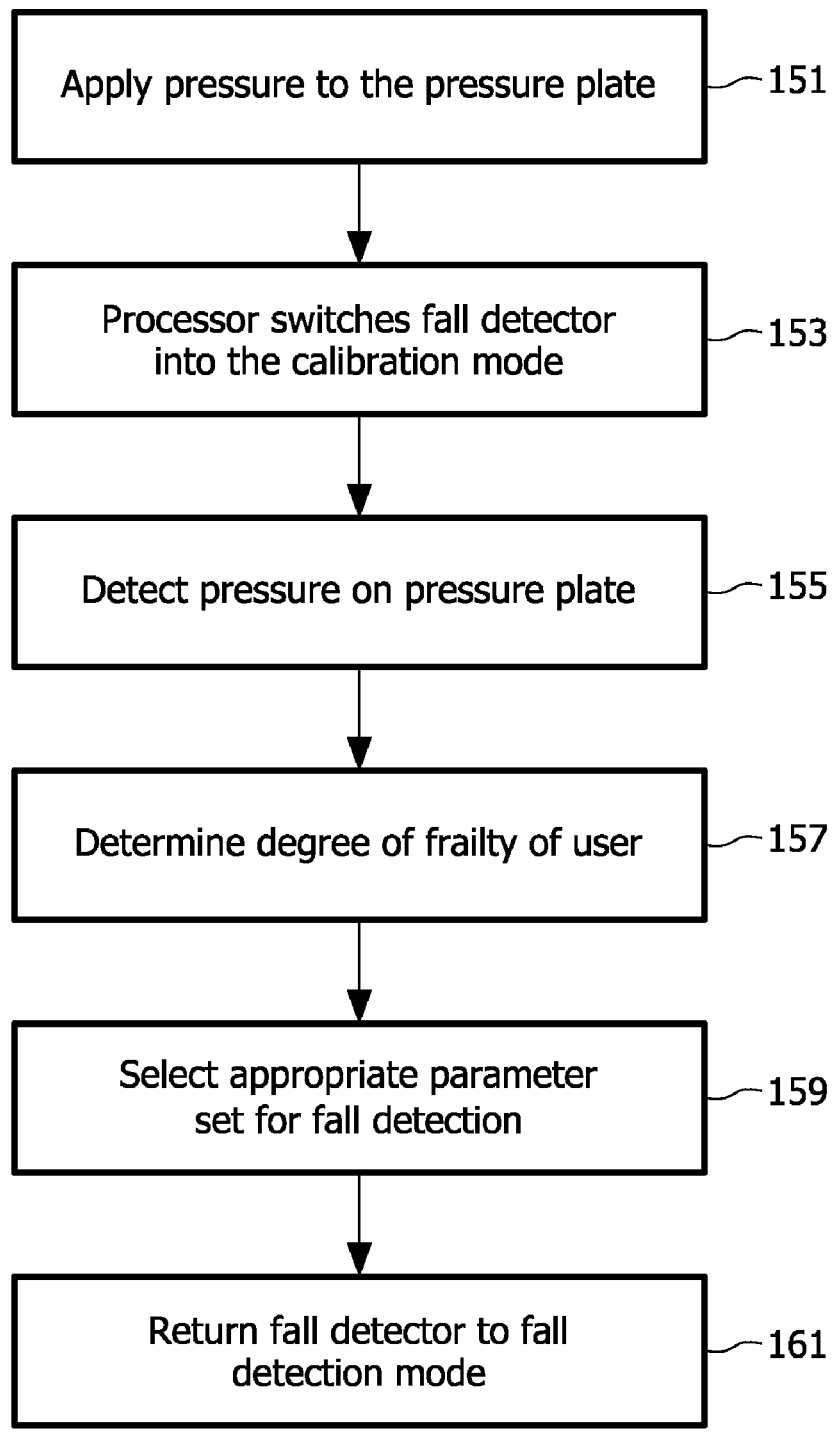
FIG. 5 shows a method in accordance with the second embodiment of the invention.

FIG. 5 shows a method of calibrating a fall detector in accordance with the second embodiment of the invention. Pressure is applied to the pressure plate on the fall detector by the user (step 151), either by directly pressing on the pressure plate with a finger, or by squeezing the fall detector. Provided that this pressure is above a predetermined threshold, the processor switches the fall detector into the calibration mode (step 153).

The fall detector then detects the pressure on the pressure plate using the pressure sensor and other physical characteristics of the user using the biosensors (step 155).

The processor then uses these measurements (or perhaps just the pressure measurement) to determine the degree of frailty of the user (step 157). For example, the frailty can be related to the maximum pressure that the user applied to the pressure sensor, which can indicate a maximum strength of the user's hand, as well as the duration for which this maximum strength was applied.

The processor can then select an appropriate parameter set for fall detection (step 159) using the results of step 157.

The processor can then return the fall detector to the fall detection mode (step 161). This may be achieved by detecting that the user is no longer pressing the pressure plate, by the user pressing the pressure plate again, or by the user pressing the personal help button.

Figure 6:
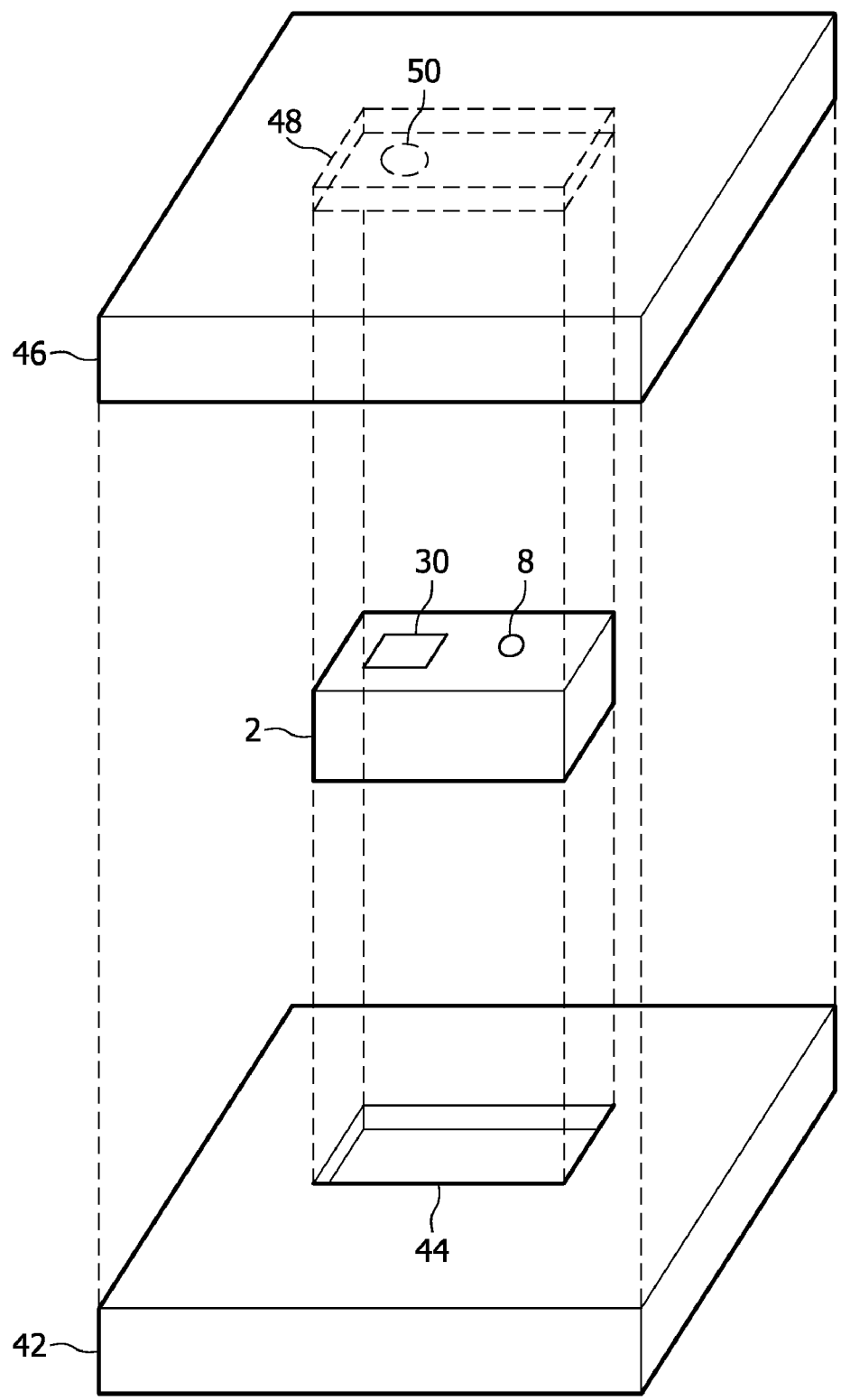
FIG. 6 shows a fall detection system in accordance with a third embodiment of the invention.

FIG. 6 shows a modification to the second embodiment of the invention, which allows the fall detector 2 to measure the weight of the user 4.

In this modification, a calibration unit 42, 46 is provided that a user can stand or sit on, and which transfers the weight of the user to the pressure plate 30. The calibration unit comprises two plates 42, 46 which are adapted to cooperate with the fall detector 2, and in particular with the pressure plate 30, such that the body weight or torso weight of a user standing or sitting on the calibration unit respectively is transferred to the pressure plate 30. In this particular embodiment, the two plates 42, 46 comprise respective recesses 44, 48 for receiving a part of the fall detector 2, with the recess 48 in the upper plate 46 including a protuberance 50 which is sized and located so as to press on the pressure plate 30 when the user stands or sits on the upper plate 46.

In an alternative to this modification, a single plate can be provided in the calibration unit for transferring the weight of the user to the pressure plate 30.

In further embodiments of the invention, the fall detection system 1 could be initially set to a calibration mode, and only switches to the fall detection mode after the initial calibration has been carried out. It is also possible for the users to update the initial measurements after a certain period of time by entering the calibration mode again.

There is therefore provided a fall detection system that is adaptable to different usage conditions (i.e. for different users), which enhances the reliability of the fall detection system by increasing detection accuracy and eliminating false positives and false negatives. The fall detection system is also simple and easy to use for an elderly user.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detection system, comprising:
a fall detector for monitoring movement of a user and detecting if the user has fallen or is about to fall; and
a calibration unit that switches the fall detector into a calibration mode, the calibration unit including one or more sensors for collecting measurements of one or more physical characteristics of the user;
wherein, during the calibration mode, the fall detector uses the measurements to adapt the fall detection to the physical characteristics of the user.

2. A fall detection system as claimed in claim 1, wherein the fall detector compares the movements of the user to a parameter set comprising one or more thresholds or patterns to detect if the user has fallen or is about to fall.

3. A fall detection system as claimed in claim 2, wherein the fall detector adapts the fall detection to the physical characteristics of the user by selecting a parameter set from a plurality of parameter sets appropriate to the measurements of the physical characteristics.

4. A fall detection system as claimed in claim 1, wherein the one or more sensors are provided in the calibration unit, the calibration unit being separate to the fall detector.

5. A fall detection system as claimed in claim 4, wherein the calibration unit is adapted to provide the measurements of the one or more physical characteristics to the fall detector.

6. A fall detection system as claimed in claim 5, wherein the calibration unit comprises a recess adapted to receive at least a part of the fall detector.

7. A fall detection system as claimed in claim 4, wherein the one or more sensors comprises a pressure sensor for measuring a body weight or torso weight of the user when the user stands or sits on the calibration unit respectively.

8. A fall detection system as claimed claim 1, wherein the calibration unit is adapted to switch the fall detector into calibration mode in which the fall detector uses the measurements to adapt the fall detection to the physical characteristics of the user when the fall detector and calibration unit are placed in contact with each other.

9. A fall detection system as claimed in claim 1, wherein the fall detector comprises the one or more sensors.

10. A fall detection system as claimed in claim 9, wherein the one or more sensors comprises a pressure sensor with an associated pressure plate.

11. A fall detection system as claimed in claim 10, wherein the fall detector measures a degree of frailty of the user when the user presses on the pressure plate.

12. A fall detection system as claimed in claim 11, wherein the fail detector measures the degree of frailty based on a maximum pressure exerted on the pressure plate by the user and/or an average pressure exerted over a period of time on the pressure plate by the user.

13. A fall detection system as claimed in claim 10, wherein the fall detector is adapted to switch into the calibration mode in which the fall detector uses the measurements to adapt the fall detection to the physical characteristics of the user when a pressure exerted on the pressure plate exceeds a threshold.

14. A fall detection system as claimed in claim 10, wherein the fall detection system further comprises the calibration unit that is adapted to cooperate with the pressure plate of the fall detector such that the pressure sensor measures a body weight or torso weight of the user when the user stands or sits on the calibration unit respectively.

15. A fall detection system as claimed in claim 1, wherein the physical characteristics comprises one or more of body weight, torso weight, height, general physical condition, a degree of frailty of the user, heart rate/pulse, blood pressure, ECG signals or other biological signals.

16. A method of operating a fall detection system, the method comprising:
- switching, by a calibration unit, the fall detection system to a calibration mode;
- collecting, in the calibration mode, measurements of one or more physical characteristics of a user of the fall detection system;
- using the measurements to adapt a detection of falls, or falls that are about to happen, to the physical characteristics of the user.

* * * * *